US009008264B2

(12) United States Patent  
Boone et al.

(10) Patent No.: US 9,008,264 B2  
(45) Date of Patent: Apr. 14, 2015

(54) APPARATUS AND METHODS FOR DETERMINATION OF THE HALF VALUE LAYER OF X-RAY BEAMS

(75) Inventors: John M. Boone, Folsom, CA (US); George W. Burkett, Jr., Davis, CA (US); Sarah E. McKenney, Sacramento, CA (US)

(73) Assignee: The Regents of the University of California, Oakland, CA (US)

(*) Notice: Subject to any disclaimer, the term of this patent is extended or adjusted under 35 U.S.C. 154(b) by 457 days.

(21) Appl. No.: 13/550,502

(22) Filed: Jul. 16, 2012

(65) Prior Publication Data

US 2013/0016808 A1 Jan. 17, 2013

Related U.S. Application Data

(60) Provisional application No. 61/508,436, filed on Jul. 15, 2011.

(51) Int. Cl.
*G01N 23/04* (2006.01)
*A61B 6/00* (2006.01)

(52) U.S. Cl.
CPC ............... *G01N 23/04* (2013.01); *A61B 6/583* (2013.01); *A61B 6/4035* (2013.01); *A61B 6/586* (2013.01); *G01N 2223/302* (2013.01); *G01N 2223/313* (2013.01)

(58) Field of Classification Search
USPC .................................... 378/51, 55, 207, 208
See application file for complete search history.

(56) References Cited

U.S. PATENT DOCUMENTS

| | | | |
|---|---|---|---|
| 4,935,950 A | 6/1990 | Ranallo et al. | |
| 6,454,460 B1 | 9/2002 | Ramanathan et al. | |
| 7,580,504 B2 | 8/2009 | Lang et al. | |
| 7,616,796 B2 | 11/2009 | Crucs | |
| 7,628,538 B2 | 12/2009 | Dehler | |
| 2004/0260331 A1* | 12/2004 | D'Aquanni et al. | 606/200 |
| 2010/0054396 A1 | 3/2010 | Warner et al. | |

OTHER PUBLICATIONS

Kruger, Randell L. et al.—"Measurement of half-value layer in x-ray CT: A comparison of two noninvasive techniques"—Med. Phys. 27 (8), Aug. 2000, pp. 1915-1919.
Mathieu, Kelsey B. et al.—"Precision of dosimetry-related measurements obtained on current multidetector computed tomography scanners"—Med. Phys. 37 (8), Aug. 2010.
Maia, Ana F. et al.—"A simple method for evaluation of half-value layer variation in CT equipment"—Phys. Med. Biol. Mar. 2006, pp. 1595-1601, vol. 51.
Kruger, Randell L. et al.—"Measurement of Half-Value-Layer in X-ray CT: A Comparison of Two Noninvasive Techniques"—Proceedings of the 22nd Annual EMBS International Conference, Jul. 23-28 2000, Chicago, IL, pp. 98-101.

(Continued)

*Primary Examiner* — Kiet T Nguyen
(74) *Attorney, Agent, or Firm* — John P. O'Banion

(57) ABSTRACT

Described is an apparatus for use in HVL measurement as well as methods of making measurements. One version of the apparatus is a cage structure having a central axis and a central opening defined by a filter encircling the central axis, with the filter having a thickness that varies peripherally around said central axis. The filter can be formed from multiple spaced-apart plates having varying thicknesses or can be formed from a cylinder having a continuously increasing thickness.

20 Claims, 10 Drawing Sheets

(56) References Cited

OTHER PUBLICATIONS

McKenney, Sarah—"Application of real-time dosimetry to characterize the x-ray penetrability of CT scanners"—American Association of Physicists in Medicine Young Investigators' Symposium Competition, Jul. 31-Aug. 4, Vancouver, Canada.

McKenney, Sarah et al.—"Experimental validation of a method characterizing bow tie filters in CT scanners using a real-time dose probe"—Med. Phys. Mar. 2011, pp. 1406-1415, vol. 38, No. 3.

Hill, A.L.—"Half value layer measurements to facilitate patient dose assessment for newer CT scanners using published normalized dose data"—The British Journal of Radiology, Aug. 1999, pp. 792-798, vol. 72.

* cited by examiner

APPARATUS AND METHODS FOR DETERMINATION OF THE HALF VALUE LAYER OF X-RAY BEAMS

CROSS-REFERENCE TO RELATED APPLICATIONS

This application claims priority from U.S. provisional patent application Ser. No. 61/508,436 filed on Jul. 15, 2011, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention pertains generally to imaging systems and methods such as computed tomography, and more particularly to methods and devices for measuring the half-value level (HVL) for imaging.

2. Description of Related Art

X-ray based imaging and other types of radiographic analysis are established diagnostic tools. The penetrating ability of photons is one of the characteristics of x-ray and gamma ray radiations that make them useful for medical imaging, for example. Photons directed at an object either completely penetrate the object or are absorbed or scattered. The amount of penetration depends on the energy of the individual photons and the atomic number, density, and thickness of the object that is being bombarded. Therefore, photon penetration can be expressed as the fraction of radiation that passes through the object and it is the inverse of attenuation.

X-ray beams used for medical purposes generally are poly-energetic i.e. the x-ray beam is comprised of a spectrum of photons with different x-ray energies. When the applied voltage (kV) between the cathode and anode in an x-ray tube is changed, the spectrum will change. The addition of metallic filters in the x-ray tube housing (or collimation structure) also changes the shape of the spectrum. Accordingly, an x-ray beam is made up of different photon energies and photons of certain energies will penetrate better than others. The low-energy photons in the x-ray spectrum will not contribute to image formation and will be absorbed or scattered by the tissue of the patient. This selective thinning of photons based on their energy by a material is referred to as filtration.

Because it is difficult to measure the actual x-ray spectrum due to the time and equipment requirements of x-ray spectroscopy, a typical metric that is used to characterize the penetrability of an x-ray beam is called the half value layer (HVL). The half-value layer (HVL) is a quantification of the penetration of the x-ray beam through a material that is being examined. HVL is defined by the thickness of a material that reduces the transmission of the x-ray beam by 50%. The units used to express the HVL are typically millimeters or centimeters and the HVL value is photon energy dependent.

Photon absorbing and filtering materials can preferentially absorb lower-energy x-ray photons emitted by the x-ray source and thereby filter the beam. The amount of filtration of the x-ray beam will depend on the voltage potential (keV) used to produce the beam and the thickness and atomic number of filter material.

Filters used in industrial radiography to filter the x-ray beam are typically made from high atomic number materials such as copper, tin, brass or lead. However, filters for medical radiography are normally made from aluminum. In diagnostic radiology, typically sheets of 1.0 mm aluminum are used as filters, but the concept is valid for any material such as copper or tin. When both the applied voltage (kV) and the HVL of a spectrum are known, an x-ray spectrum is well characterized. Most x-ray systems used for medical imaging have the ability to adjust the kV, and thus it is common practice amongst medical physicists to characterize the x-ray system by measuring the HVL at three or more kV settings.

The practice of measuring the HVL, in general, proceeds with a radiation meter (which measures x-ray beam exposure in the units of roentgens or air kerma in the units of mGy) that is positioned to measure a collimated (narrow) beam of x-rays from the source, and serial measurements are made.

The thickness of the aluminum sheets is changed between measurements by adding an additional sheet of Al. Depending on the x-ray spectrum, the beam will be attenuated differently by the added aluminum filters. HVL values typically run from about 0.25 mm of Al in mammography to 9 to 12 mm Al in computed tomography (CT) at high kV.

The half value layer is defined as the thickness of added material (aluminum is the most typical, however this material can be any metal or compound) which results in the attenuation of the initial x-ray beam (when t=0) to 50%. Mathematically, the HVL can be defined as:

$$0.500 = \frac{\int_{E=E_{min}}^{E_{max}} k(E)\, \Phi(E)\, e^{-\mu_z(E) \times HVL}\, dE}{\int_{E=E_{min}}^{E_{max}} k(E)\, \Phi(E)\, dE}$$

The HVL is measured by medical physicists for x-ray beams including fluoroscopy, radiography, mammography, and in computed tomography (CT). Calculation of the HVL of an x-ray based system is usually performed for two related purposes: 1) apparatus quality assurance; and 2) radiation dose reduction in imaged patients.

Image quality is essential to a proper diagnosis and requires that the x-ray generator work under reproducible conditions. Because low energy photons do not contribute to the formation of the image and rather contribute only to the radiation dose of the patient, diagnostic x-ray equipment includes a minimum filter so that the apparatus produces a beam of a standard quality.

Since ionizing radiation can cause damage to tissues, minimizing x-ray exposure reduces the risk of injury to the patient. Therefore, consistent x-ray beam characteristics minimize the risk of excess exposure.

HVL values may also be used as a preventive indication of equipment malfunctions. Many states in the United States require HVL determinations of an x-ray beam as a standard quality assurance test for radiographic and fluoroscopic systems. If a system is not in compliance with the expected standards, corrective action may need to be taken and servicing of the equipment performed.

In addition to its utility as a quality assurance tool, the HVL of an x-ray based system is a useful indicator of the relative "hardness" of the x-ray beam. Along with the known x-ray tube voltage (kV), the HVL is a useful metric which is used extensively in the field of medical physics to describe the "hardness" of an x-ray beam. Higher energy x-ray beams are considered "hard" and penetrate objects (such as the patient) more readily than softer (lower energy) x-ray beams. HVL is also an indicator of how much soft radiation is present in the beam. Soft radiation is absorbed in the surface tissue and does not contribute to formation of the image. Image quality can be maximized and the radiation dose minimized by HVL monitoring and device calibration.

BRIEF SUMMARY OF THE INVENTION

The present invention is an apparatus for use in producing half value layer measurements as well as methods for making accurate HVL measurements. By way of example, and not of limitation, the apparatus generally comprises an x-ray source that provides a beam directed at a cylindrical cage structure having a central axis and a central interior opening defined by filter elements encircling the central axis and support walls, with the individual filter elements having a thickness that vary.

The apparatus can include a probe holder configured to retain at least a portion of a radiation probe within the central opening of the cage and along the central axis of the cage. The radiation sensor is preferably at the center of the cage. However, the sensor may also be on the outside of the cage directly opposite the x-ray beam.

The cage can be configured to remain stationary in a diagnostic or therapy apparatus, or the cage can be configured to rotate within a diagnostic or therapy apparatus. Similarly, the x-ray source can be stationary or configured to circle the cage at an equal distance from the central axis of the cage. For example, the filter elements can comprise a plurality of spaced-apart plates having varying thicknesses. Plates are preferably within the range of approximately 0.1 mm to approximately 15 mm in thickness and made from aluminum, copper or tin. For example, aluminum may be used as the material used for fabricating the filter (plates or cylinder). Alternatively, for measuring the HVL of a radiation therapy beam, for example at 6 MV instead of 140 kV max as in CT, copper would preferably be used instead. Furthermore, in what is called "Tomotherapy" the stationary (CT) HVL cage would be preferable, while for linear accelerators (e.g. 6-18 MV), a rotary system would be good as with radiography.

The plates that are placed circumferentially on the support walls of the cage may be placed singly or in multiples, such as ranging from approximately five to approximately ten plates or more. The plates in the cage can be placed in order of increasing thickness or the order of plate thickness can be random. The plates can also have a planar surface or an arcuate surface.

The typical HVL values observed in CT, radiography and fluoroscopy (R & F), and mammography vary dramatically. For example, HVL values seen in CT settings range from approximately 4 mm to approximately 12 mm of aluminum. In the case of R & F, the typical HVL ranges between approximately 2.8 mm and approximately 8.0 mm of aluminum (Al). With mammography, the HVL numbers range from approximately 0.25 mm to approximately 0.8 mm of Al. Thus, one embodiment of the HVL cage system is to have a set of different cages with different filtration thicknesses, suitable to the modality of interest, that are interchangeable. In addition, for mammography, the type of aluminum may be different, because the low energies in mammography require a purer Al alloy. Having interchangeable HVL cages would enable the same system to work for all x-ray modalities.

The shape of the cross section of the cage can permit the circumferential plates to be arranged in various patterns, such as hexagonal, octagonal, circular and other patterns. One embodiment of the HVL cage uses a large number of different filter plate thicknesses around the 360° circumference, which would result in a comprehensive measurement of Al attenuation of the x-ray beam. Alternatively, the filter can comprise a cylinder having walls with a continuously increasing thickness instead of using a polygonal frame of plates.

In another embodiment, the HVL cage is disposed at the center of the axis of rotation of a CT scanner, where the x-ray source rotates around the cage and the radiation meter is at the central axis of the scanner. As the x-ray source rotates around the cage, the x-ray beam interrogates different thicknesses of aluminum or other metal plates before striking the radiation meter.

By replacing one of the filter element sheets of metal with a small rod of lead or tungsten, the signal can be greatly attenuated due to the density and atomic number of these materials, and would be driven to near zero. This can be used to produce a synchronization point on the signal trace, to assure proper phase alignment of the known thicknesses of Al or other metal.

The diameter of the HVL cage can vary but the proximity of the filter and the probe can lead to x-ray scatter contamination in the measurements. A larger diameter HVL cage increases the separation between the filter elements and the probe reducing scatter contamination, but the cage is bulkier in size.

In one embodiment, highly attenuating septa can be added to the cage in a manner which reduces the scatter cross talk between the unused metal plates and the detector. The septa are generally perpendicular to the plates and radiate toward the central axis and radiation probe and provide a channel with a plate at one end. In another embodiment for scatter reduction in the signal measurement, the septa are angled in a preferred embodiment and the metal plates are much smaller in terms of arc angle.

In the case of the CT adaptation, the x-ray source rotates and so the HVL cage can be stationary. The HVL cage should remain stationary in the z-axis of the CT scanner during gantry rotation. One way to make this simple and not have to deal with inadvertent patient table motion is to mount the HVL cage hardware (laptop, etc.) onto a small cart that can be positioned from the back of the CT gantry.

For projection x-ray imaging such as fluoroscopy, radiography, and mammography, the x-ray source is stationary during exposure and so the HVL cage can be rotated using a stepper or other suitable motor/gear arrangement. When used for projection imaging, a static collimator can be used instead of the septa mentioned earlier to reduce the x-ray scatter contribution to the measured signal trace due to the static position of the x-ray beam.

X-ray beam quality is a key factor to consider when estimating the dose that will be received a patient. Unfortunately, beam quality is difficult to directly measure on current commercial clinical CT scanners. The present invention provides a noninvasive method to measure the half value layer (HVL) of a clinical CT scanner using a real-time dose probe and HVL apparatus. Using the HVL apparatus, measurements of HVL can be made on a CT scanner in a single rotation of the gantry. This method allows medical physicists to independently and easily conduct routine HVL measurements.

To improve the probe results and the accuracy of the calculated HVL, a corrective algorithm may be applied. Because of the physical geometry of the HVL cage, there are some apparatus-specific corrections that may be made after the signal is acquired. There are two features that are observed that may need to be corrected: (A) the sinusoidal modulation due to the inverse square law and (B) small "hills" in the attenuated portions of the signal due to parallax of the planar aluminum plates.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus and methods generally illustrated in FIGS. 1A through FIG. 11. It will be appreciated that the methods may vary as to the specific steps and sequence and the system architecture may vary as to structural details without departing from the basic concepts as disclosed herein. The method steps are merely exemplary of the order that these steps may occur. The steps may occur in any order that is desired, such that it still performs the goals of the claimed invention.

Figure 1A:
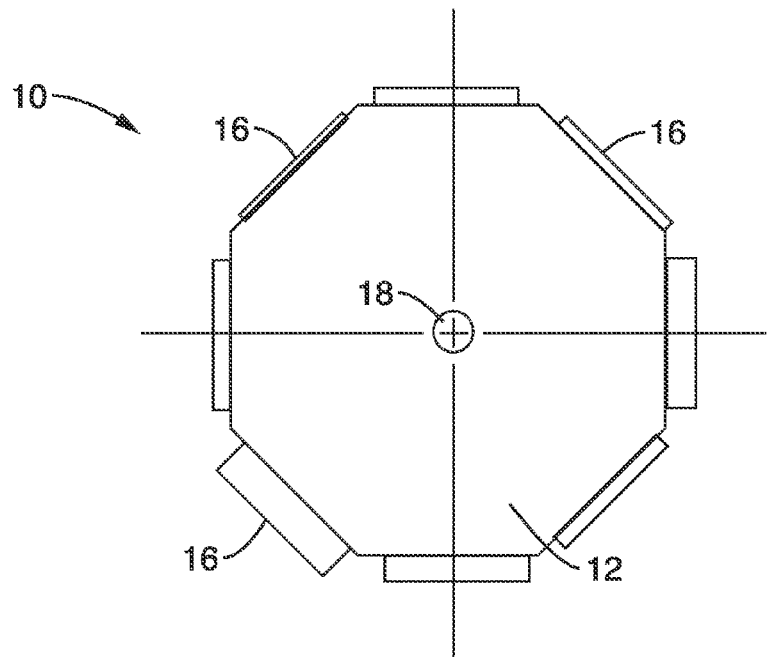
FIG. 1A is a schematic diagram showing a top view of one embodiment of the HVL "cage" according to the invention.
Figure 1B:
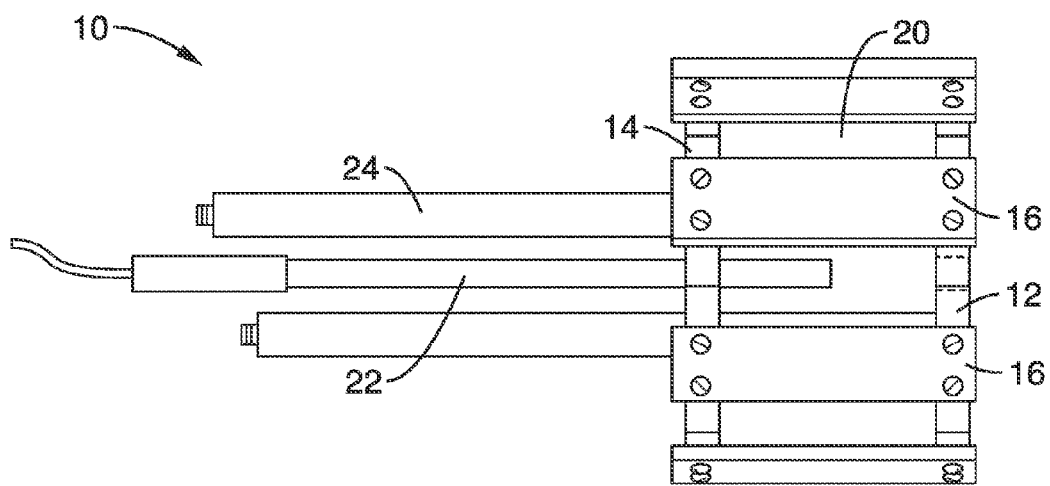
FIG. 1B is a schematic side view of the HVL cage embodiment of FIG. 1A with a real time probe in the center of the cage.

Turning first to FIG. 1A and FIG. 1B, an embodiment of a simple HVL cage structure 10 that is part of a fluoroscopy, radiography, mammography, computed tomography (CT) or other x-ray based imaging system according to the present invention is schematically shown. The embodiment of the HVL "cage" shown in FIG. 1A and FIG. 1B has a support structure that is formed from a first support wall 12 and second support wall 14. A plurality of spaced-apart filter plates 16 are positioned between the walls 12, 14 and radially arranged around a central axis 18 to form a cage-like structure with a central interior 20 defined by the filter plates 16 encircling the central axis 18 and the support walls. The plates shown in FIG. 1A are arranged on a support walls 12, 14 that have an octagonal pattern as shown, but it will be understood that the support walls could be different shapes with any reasonable number of sides, such as five to twelve. In another embodiment, the support walls 12, 14 are circular with twenty to thirty filter plates 16 that form a cylindrical cage structure. The support walls 12, 14 are preferably fabricated from stainless steel or carbon fiber.

A radiation meter (probe) 22 is disposed in the center of support wall 14 along the central axis 18 in the interior 20 of the cage. A beam of x-rays from an x-ray source is directed through a plate 16 and the photons traversing the plate 16 are detected by the radiation meter 22 during use. The radiation probe 22 is preferably disposed along the central axis of the cage.

The plates 16 are preferably made from sheets of aluminum, copper, or tin. The type of material can be selected based on the type of imaging application. For example, the type of aluminum that is used for HVL measurements for mammography needs to be much purer than the aluminum filters used for radiography or CT. In the latter, type 1100 aluminum is conventionally used. This alloy is pure enough for good Al measurements and is reasonably priced and relatively hard. For mammography, a purer Al alloy, such as type 1145, which is 99.999% Al, is required due to the low energies used in mammography. Therefore, one embodiment of the HVL cage system has a set of different cages with different filtration thicknesses, suitable to the modality of interest. This embodiment of interchangeable filter assemblies allows the addition of the different alloy of aluminum for the mammography application and a different filter assembly with different metals and thicknesses for another application.

The filter plates 16 vary in thickness and are mounted peripherally around central axis 18 as illustrated in FIG. 1A, and the thickness of the plates can vary randomly or applied in an ordered fashion. The thickness of the plates preferably ranges from approximately 0.1 mm to approximately 15 mm. The plates 16 may also be composed of several plates aligned on top of each other and mounted to the support walls 12, 14 to give a very wide range of possible plate thicknesses. Plates 16 may be the range of 10 mm to 15 mm in thickness other some configurations. In one embodiment, the top surface of the plate is arcuate rather than planer.

Figure 5A:
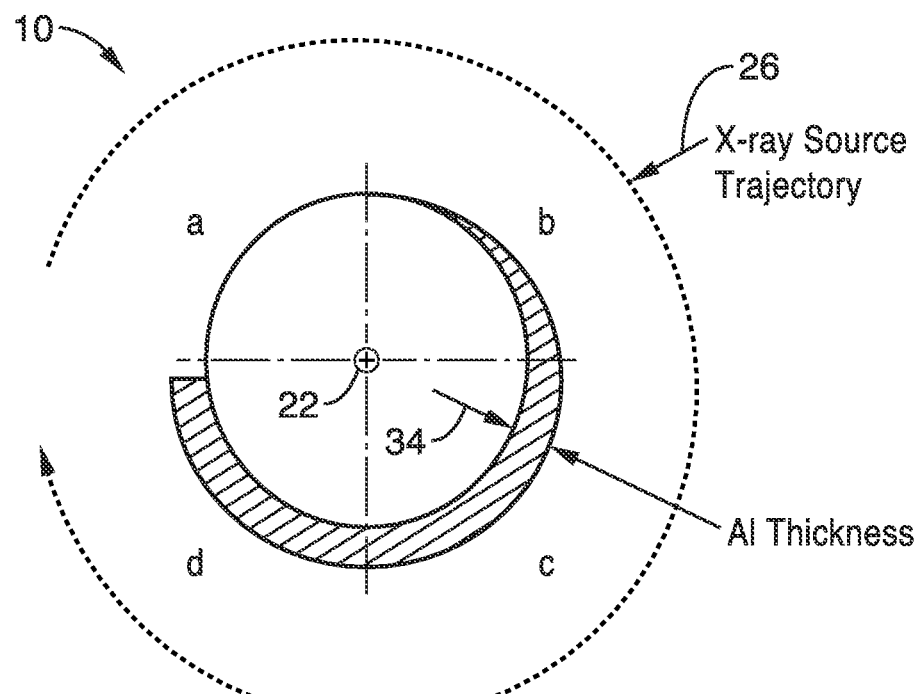
FIG. 5 is a schematic diagram of a second alternative cage embodiment showing that, instead of using a polygonal frame and flat metal plates, the cage comprises a metal cylinder of continuously increasing thickness placed in the x-ray beam path that may or may not include septa.
Figure 5B:
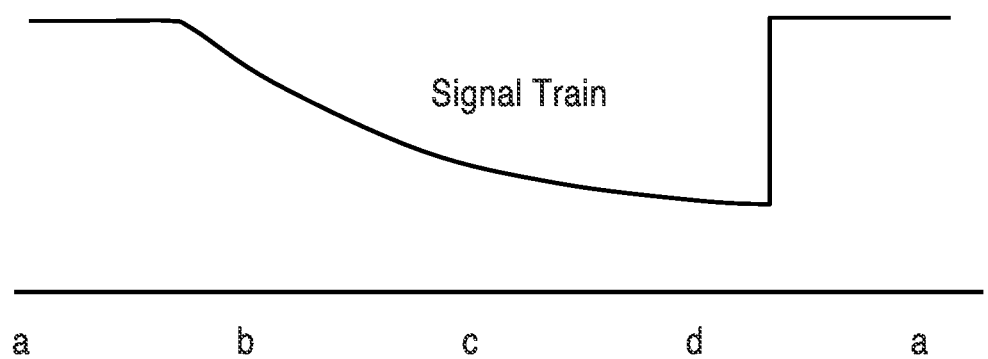

In another embodiment, the circumference of the support walls 12, 14 has plates 16 that successively increase in thickness around the circumference. Alternatively, the filter plates 16 could be replaced with a cylinder with continuously increasing thicknesses as seen in FIG. 5A and FIG. 5B. In some settings a more random order as shown in FIG. 1A may be preferred because measurement bias (e.g. detection biases in the probe or output drift in the x-ray system) may contribute to a systematic bias that would be masked by an ordered array of metal plate 16 thicknesses, but would appear as random noise (better in this case) with a random order of plate 16 thicknesses.

The HVL cage apparatus 10 can be stationary or rotating in an overall system depending on its particular use. The embodiment shown in FIG. 1B has arms 24 that are mounted to the cage support wall 14 that can be coupled to a motor and controller to allow rotation of the cage 10 to a particular position or rotation at a desirable speed.

Figure 2:
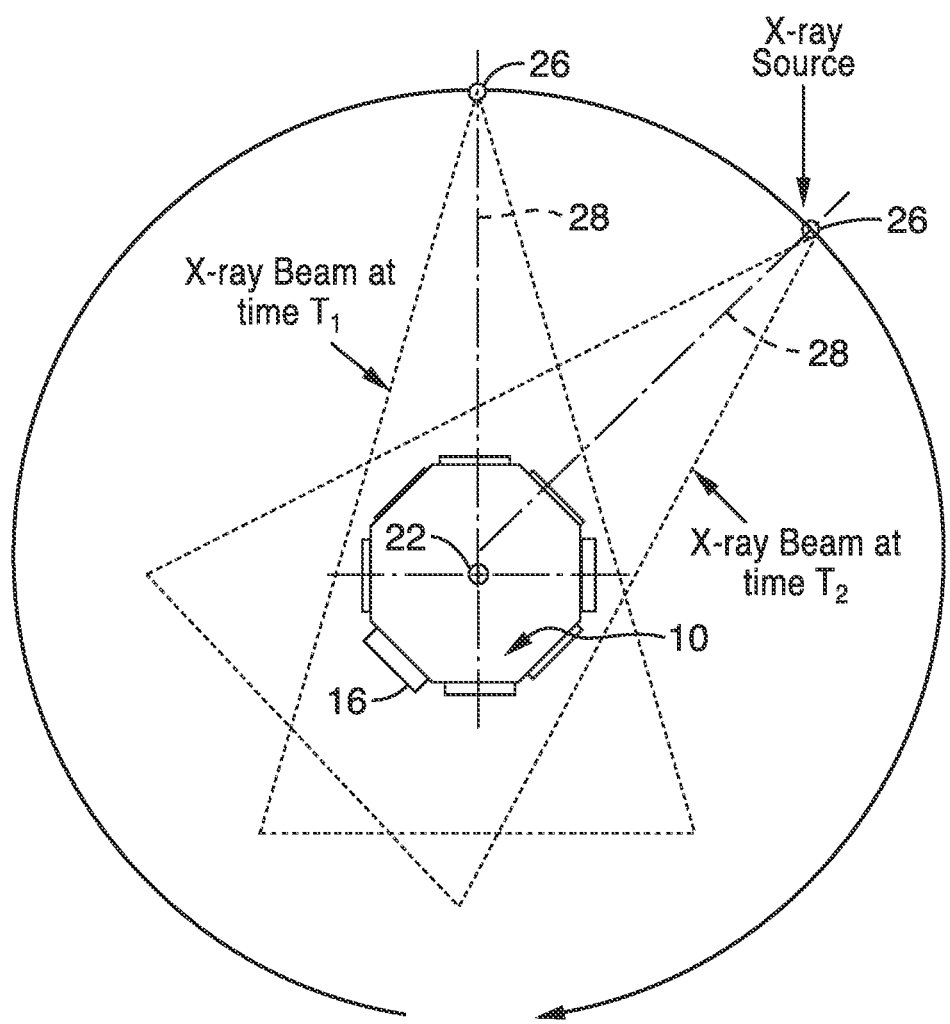
FIG. 2 is a diagram showing the HVL cage at the center of the axis of rotation of a CT scanner, where the x-ray source rotates around the cage and radiation meter. As the x-ray source rotates around the cage, the x-ray beam interrogates different thicknesses of metal plates before striking the radiation meter.

The stationary cage and moving x-ray source configuration can be illustrated with computed tomography. FIG. 2 illustrates the HVL cage 10 at the center of a CT scanner, where the x-ray source 26 rotates around the apparatus and attached radiation meter 22. Although two different x-ray beam 28 locations are shown in FIG. 2 (at time 1 and time 2), the x-ray source 26 rotates continuously around the gantry on most whole body CT scanners, with a period of rotation ranging from about 0.33 sec to 2.0 sec. During a full 360° rotation of the x-ray source 26, each of the different filter 16 thicknesses will be interrogated. In the embodiment shown in FIG. 2 there are air spaces between each metal sheet 16 and the unattenuated x-ray beam strikes the radiation meter as a consequence. To accommodate the rapid rotation of modern x-ray gantries, (0.33 sec to 0.50 sec are typically the minimum rotation period for most modern CT scanners), the radiation meter 22 needs to sample the radiation intensity very rapidly. For example, for a 330 ms gantry rotation time and to get 500 x-ray intensity measurements around 360°, the x-ray probe 22 needs to make 1500 measurements per second (corresponding to a bandwidth of 1.5 kilohertz).

A signal trace generated by the real-time radiation meter as a function of time can be measured and plotted. The signal trace is then analyzed and the relative attenuation of each known thickness of each metal plate 16 can be determined and the data can then be used to estimate the HVL. Repeated measurements with multiple rotations can be used to identify the starting point of the x-ray signal and also to make redundant measurements to improve precision.

Because there is a gap between each of the metal plates 16 on the HVL cage illustrated in FIG. 2, the x-ray signal 28 is unattenuated between the plates 16 and hence returns to the "air" or "$I_o$" measurement, and has an amplitude that is identified as $M_o$.

The amplitude $M_2$ shows the x-ray intensity for the second plate on the HVL cage. The relative attenuation (A) of the second plate (of known Al thickness) is given by:

$$A_2 = \frac{M_2}{M_o}$$

By evaluating the relative attenuation of all n aluminum plates ($A_1$-$A_n$), and knowing the corresponding aluminum thicknesses of each plate, the attenuation curves can be computed. From these curves, the HVL values can be determined in a straightforward manner, either graphically or using an interpolation algorithm.

The x-ray beam on most commercial whole body CT systems turns on at arbitrary angles, and thus the user does not have control of exactly what angle the beginning of the signal will start. Indeed, because CT scanners in helical mode can rotate a large number of times, the most typical embodiment of the HVL measurement method will be to measure a real time signal for several rotations of the scanner, getting repeated measurements to reduce noise and assure better precision.

By replacing one of the sheets of aluminum with a small rod of lead or tungsten, the signal would be greatly attenuated due to the density and atomic number of these materials, and would be driven to near zero. This can be used to produce a synchronization point on the signal trace, to assure proper phase alignment of the known thicknesses of metal plate 16. Another embodiment of the apparatus can include a small rod of highly attenuating material such as lead or tungsten on the cage structure to generate a synchronization mark on the signal trace which can be used by automated software to align the signal trace with the known array of aluminum thicknesses.

It is well known that "narrow beam" geometry should be used for making HVL measurements. Narrow beam geometry attempts to eliminate most of the x-ray scatter contamination from reaching the radiation meter. The typical diameter of the typical CT x-ray tube path shown in FIG. 2 is approximately 100 cm. Smaller HVL cage structures with approximate diameter of 15 cm are compact but there is more x-ray scatter contamination in the measurement due to the proximity of the filter and probe. When the Al filters are placed closer to the radiation meter, scatter from peripheral areas on the filter have a higher probability of reaching the radiation meter and skewing the signal, due to solid angle reasons. A larger diameter HVL cage increases the separation between filters 16 and probe 22, reducing scatter contamination by reducing the solid angle with which scatter can reach the probe. The trade off is that the larger diameter HVL cage is bulkier, larger, and heavier due to additional support structure.

Figure 3:
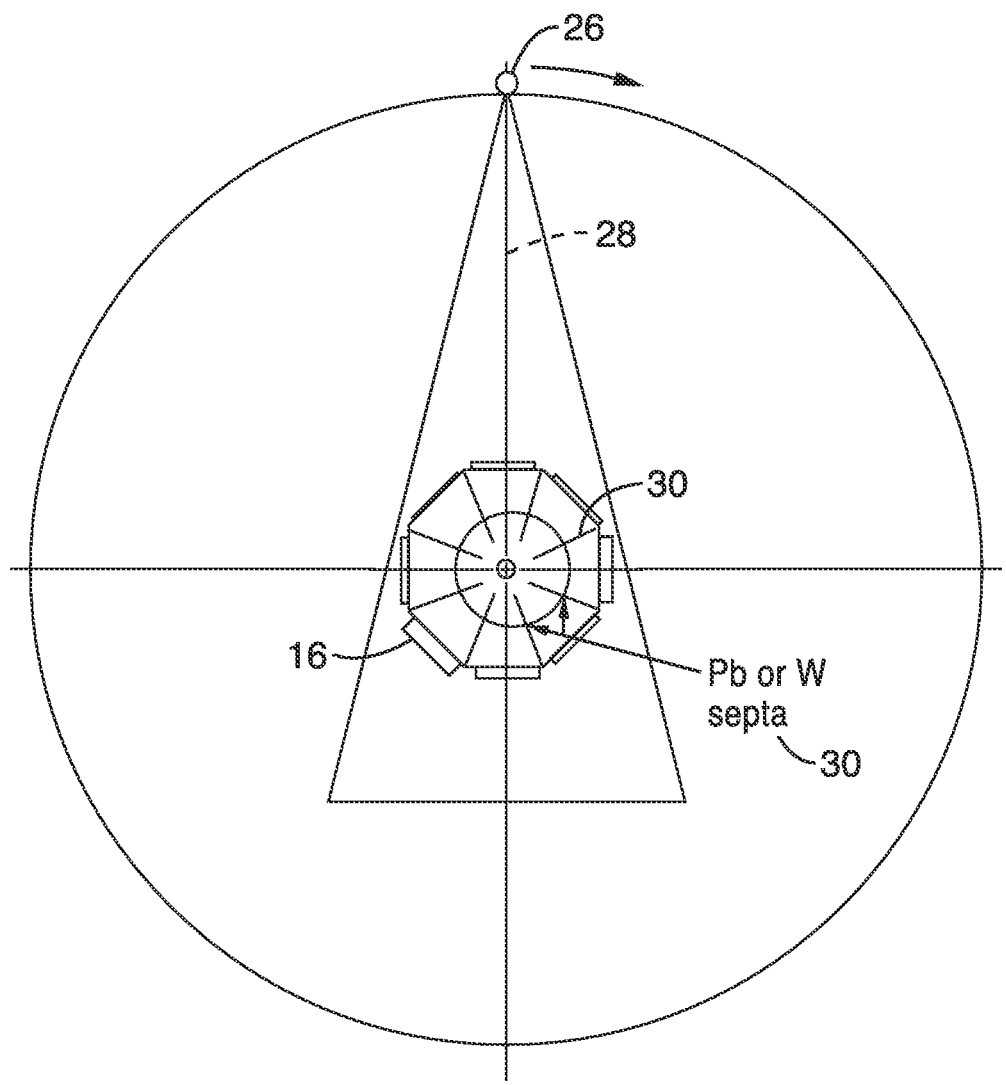
FIG. 3 is a schematic diagram of an alternative embodiment of a cage showing that highly attenuating septa can be added to the cage in a manner which reduces the scatter cross talk between the unused metal plates and the detector according to an embodiment of the invention.

Another method for reducing the scatter contribution to the measured signal trace is to use highly attenuating (e.g. Pb or W, etc.) septa 30 in the HVL cage 10 to attenuate scattered radiation geometrically from reaching the radiation detector 22. One embodiment of the HVL cage 10 incorporating septa 30 is shown in FIG. 3. The septa 30 generally form an insulating channel with a plate 16 at the distal end and the radiation probe 22 at the other.

Figure 4:
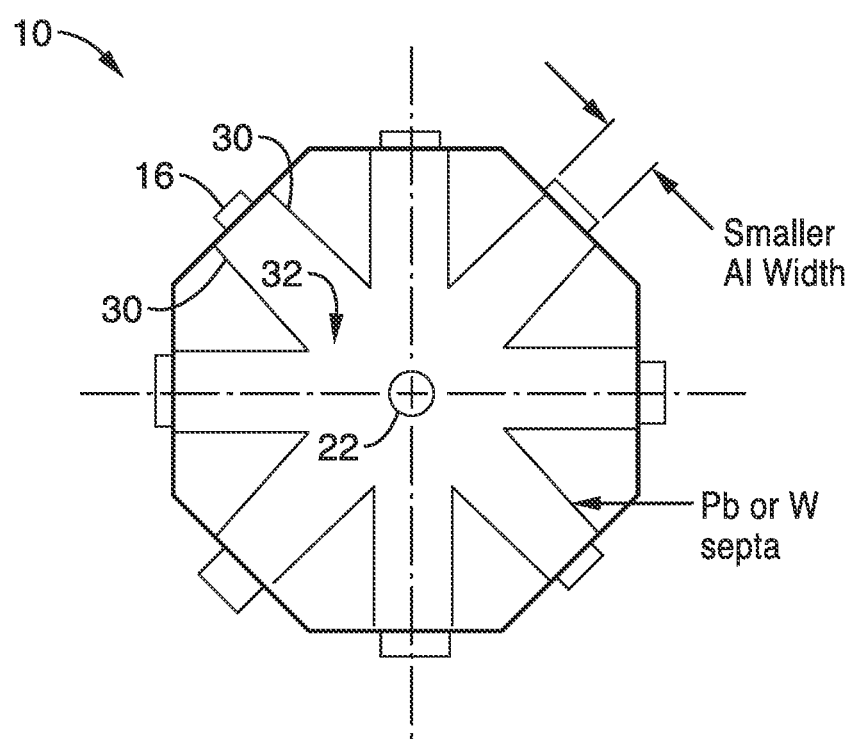
FIG. 4 is a schematic diagram showing an alternative cage embodiment of the invention for scatter reduction in the signal measurement. The septa are angled in a preferred embodiment and the metal plates are much smaller in terms of arc angle.

FIG. 4 shows an alternative HVL cage 10 embodiment using septa 30 to attenuate scattered radiation encountered by the probe 22. In this embodiment, the plates 16 are narrower and the corresponding channel 32 formed by the septa 30 is also narrower producing a smaller arc angle.

An alternative cage embodiment is shown in FIG. 5A and FIG. 5B. Unlike the HVL cage design that is a series of metal plates of differing thickness, the cage 10 is a cylinder that has walls 34 with increasing thickness from one point on the circumference to another. A beam from an x-ray source would encounter a wall 34 with different thicknesses as it followed the circular trajectory. FIG. 5B illustrates the signal train received from radiation probe 22 as the circling beam impinges on the wall 34. This design would require more precise fabrication of the metal attenuator, but one advantage is that the temporal response of the radiation meter could be of lower bandwidth because abrupt (high frequency) changes in the signal trace do not occur except at a reset (synchronization) point.

Figure 6:
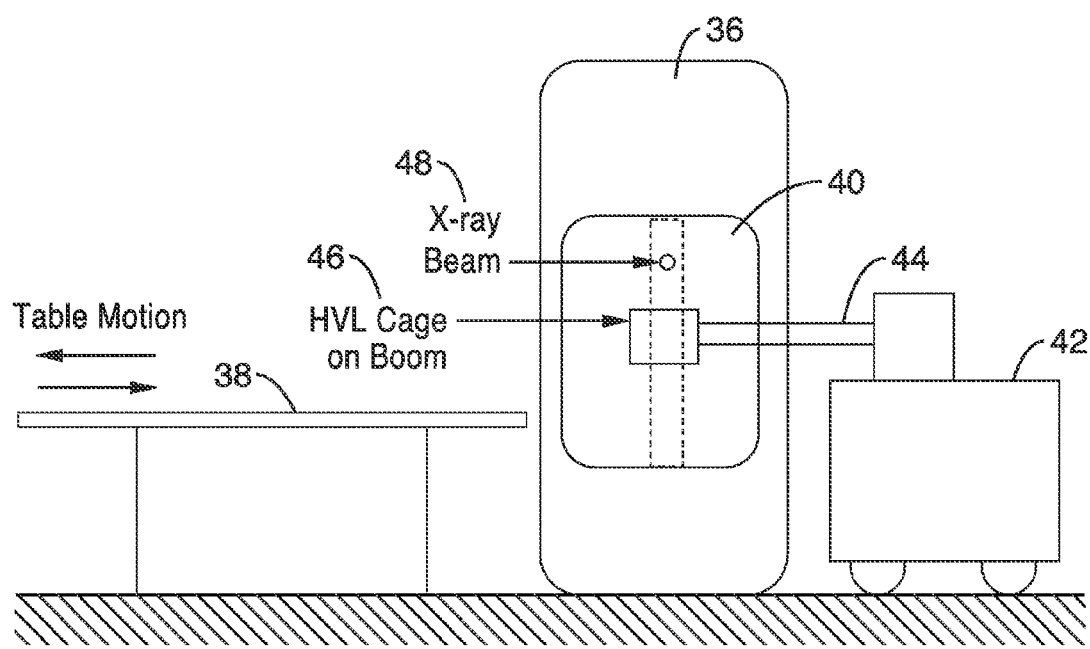
FIG. 6 is a schematic diagram showing that, in one embodiment of the invention, the HVL cage remains stationary in the z-axis of the CT scanner during gantry rotation. In order to avoid inadvertent patient table motion, the HVL cage hardware (computer, etc.) is mounted onto an optional small cart that can be positioned from the back of the CT gantry.

Turning now to FIG. 6, an alternative embodiment adapted for use with a conventional CT scanner 36 is schematically shown. The HVL cage concept in a CT scanner 36 requires that there be no other object in the scanner's field of view, and in particular this means that the patient table 38 needs to be retracted while using the HVL device. In this way, the attenuation of the table 38 will not interfere with the attenuation measurements made by the HVL device. The use of the HVL cage 46 for a series of rotations requires that the CT scanner be operated in helical (also called spiral) mode, and in some CT scanners this may require that the table actually move, even if it is positioned outside the scanner's field of view. Thus, the CT table 38 is normally not an ideal platform for positioning the HVL cage apparatus on during HVL measurements in a CT scanner 36.

All commercial whole body CT scanners provide access in openings 40 on one or both sides of the gantry. These openings provide the opportunity to use a mobile platform 42 that is separate from the CT hardware to mount and position the HVL cage within the CT x-ray beam, as shown in FIG. 6. The cart 42 can also contain a laptop computer which in general will receive the output from the radiation detector, power supplies, and other optional components of the HVL cage assembly. The cart 42 need not be bulky, but should provide an extension boom 44 to hold the HVL cage 46 that can be moved in three orthogonal directions to allow optimal alignment of the HVL cage 46 with respect to the x-ray beam 48. It is desirable to place the radiation probe at the center of the HVL cage 46 at the isocenter of the x-ray beam rotation, and all CT scanners have laser lights which would aid in such positioning.

As seen in FIG. 2, FIG. 3 and FIG. 6, the x-ray source in a CT scanner rotates in a defined trajectory and that fact is exploited such that a static HVL cage can be used to make attenuation measurements with different metal filter thicknesses. For CT scanners the HVL cage 10 requires no moving parts.

However, for the estimation of HVL in situations where the x-ray source 50 does not move, as in radiography, fluoroscopy and mammography, motion of the HVL cage would be required. Therefore, in these settings the cage itself can be mounted on a slip-ring and a motor 56 such that the metal filter cage structure 54 rotates during the exposure time constraints of projection imaging.

Figure 7:
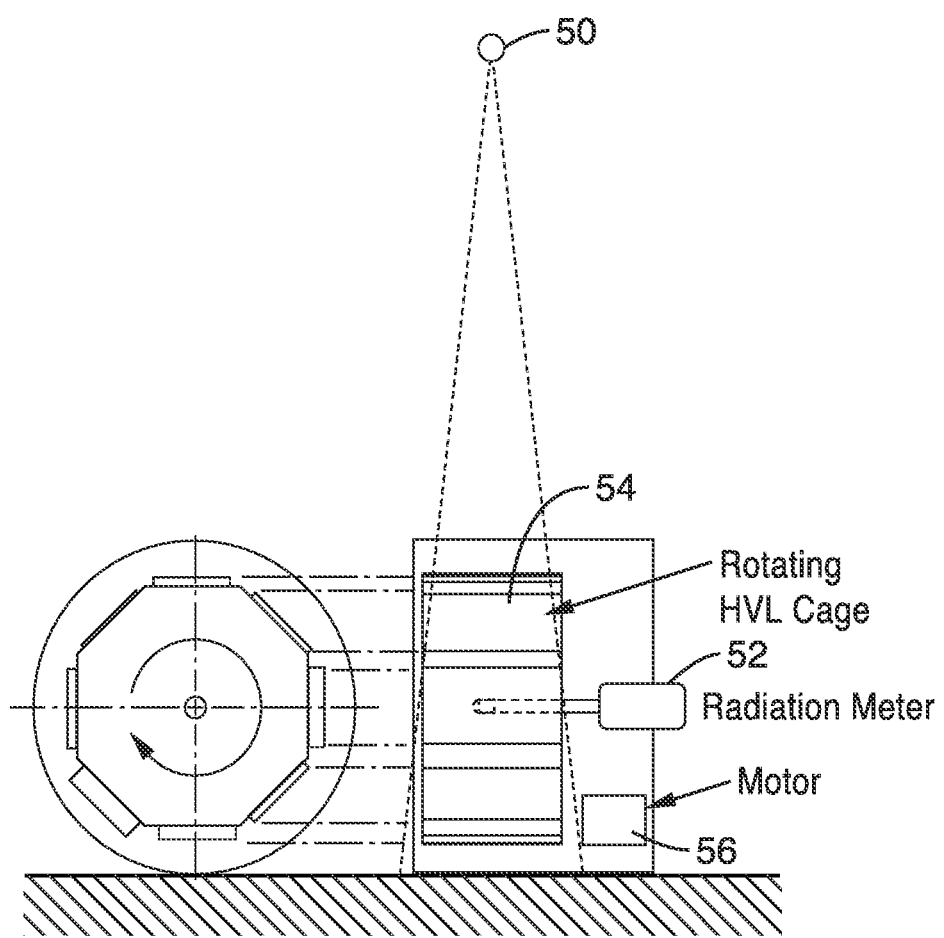
FIG. 7 is a schematic diagram configured for HVL measurements in radiography, fluoroscopy, and mammography systems where the HVL cage rotates. In CT, the x-ray source orbits around the cage so the HVL cage can be stationary. For projection x-ray imaging such as fluoroscopy, radiography, and mammography, the x-ray source is stationary during exposure and so the HVL cage can be rotated using a stepper or other suitable motor/gear arrangement.

One embodiment of the system with a rotating cage is illustrated in FIG. 7. The radiation probe 52 can be stationary or be a part of the rotating frame. If the detector 52 rotates, however, the cable will become twisted after some turns of the cage 54 and therefore some cable management system would need to be included. To avoid this, the preferred embodiment is designed to have the radiation detector 52 remain stationary while the metal filters of the cage 54 rotate around it during the measurement.

In projection radiography settings (which includes radiography, fluoroscopy, and mammography), the HVL apparatus would normally be located on top of the x-ray detector panel with the x-ray beam 50 oriented vertically and facing down. It is typical to protect the x-ray detector when making repeated physics measurements on radiological equipment, and therefore the base of the HVL cage apparatus for projection imaging may have an optional attenuating plate which protects the imaging detector underneath from repeated, intense, x-ray exposures.

Figure 8:
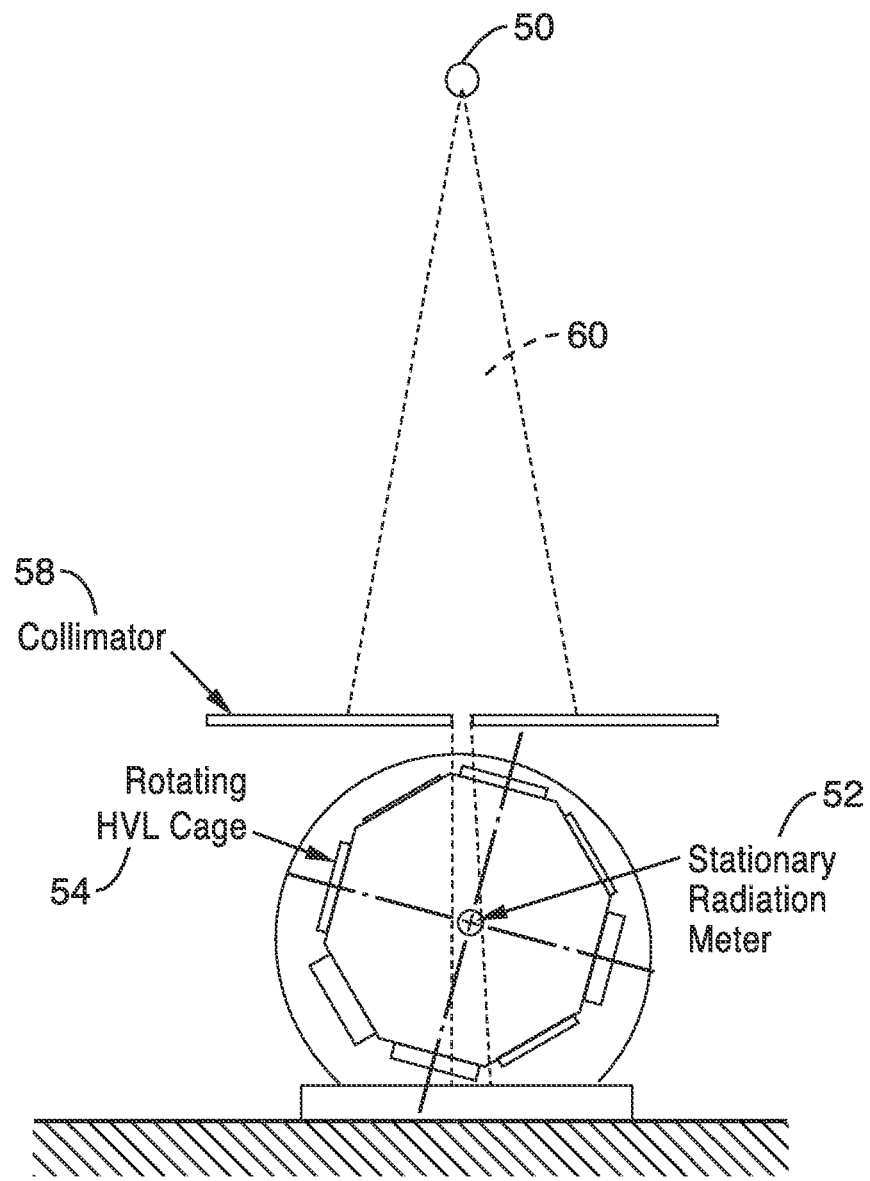
FIG. 8 is a schematic diagram showing an alternative embodiment for HVL measurements in radiography, fluoroscopy, and mammography systems where the HVL cage rotates. When used for projection imaging HVL assessment, due to the static x-ray beam position, a static collimator can be used instead of the septa to reduce the x-ray scatter contribution to the measured signal trace.

The stationary x-ray source geometry of projection radiography also allows the use of a static collimator assembly with the HVL cage apparatus, as shown in FIG. 8. The collimator 58 can reduce the width of the x-ray beam 60 from x-ray source 50 and this preserves "good" geometry and reduces the contribution of scattered radiation to the radiation meter.

For HVL measurement, it is important that the measurement data include physical metal filter thicknesses which straddle the to-be-measured HVL. For example, for an x-ray beam that has an HVL of 5 mm Al, it would be ideal to have measured attenuation data points at 0 mm added filter (always necessary), and with (for example) 4.8 mm and 5.2 mm thick Al filters. In this way, the calculation of the HVL value from the measured data points is performed with measurements on either side of the interpolated value. Extrapolation of the HVL values from incomplete attenuation measurements is to be avoided. All of this simply means that the thicknesses of metal filter plates 16 need to be adaptable to the type of x-ray beam being measured. CT scanners use high energy x-ray beams with lots of inherent filtration, resulting in typical HVL's ranging from 4 to 12 mm (in general). On the other extreme, in mammography, the kV is very low and the HVLs range from 0.25 mm to 0.8 mm of Al. Radiography and fluoroscopy systems typically employ x-ray beams with HVLs which can range from 2.5 mm Al to 8.0 mm Al.

To accommodate these different filtering needs, in one embodiment, the actual filter assembly of the HVL cage is interchangeable, and three or more possible filter assemblies could be provided for selection by the user. The use of three or so interchangeable filter assemblies in the HVL cage apparatus enables the use of the device for all x-ray modalities commonly used in a radiology department, while still maintaining a small number of overall measurements which are made around the 360° rotation of the HVL cage. For example, from 5 to 10 individual metal filter plates should be adequate on each filter assembly.

Another embodiment which addresses this issue avoids interchangeable filter assemblies, with the use of an HVL cage with a large number of metal plate 16 thicknesses. By increasing the number of metal plate filters on the HVL cage, a larger range of plate thicknesses can be measured. However, given the large dynamic range of HVL values in radiological beams a single filter assembly approach may be more expensive to implement than multiple interchangeable cages.

Figure 9:
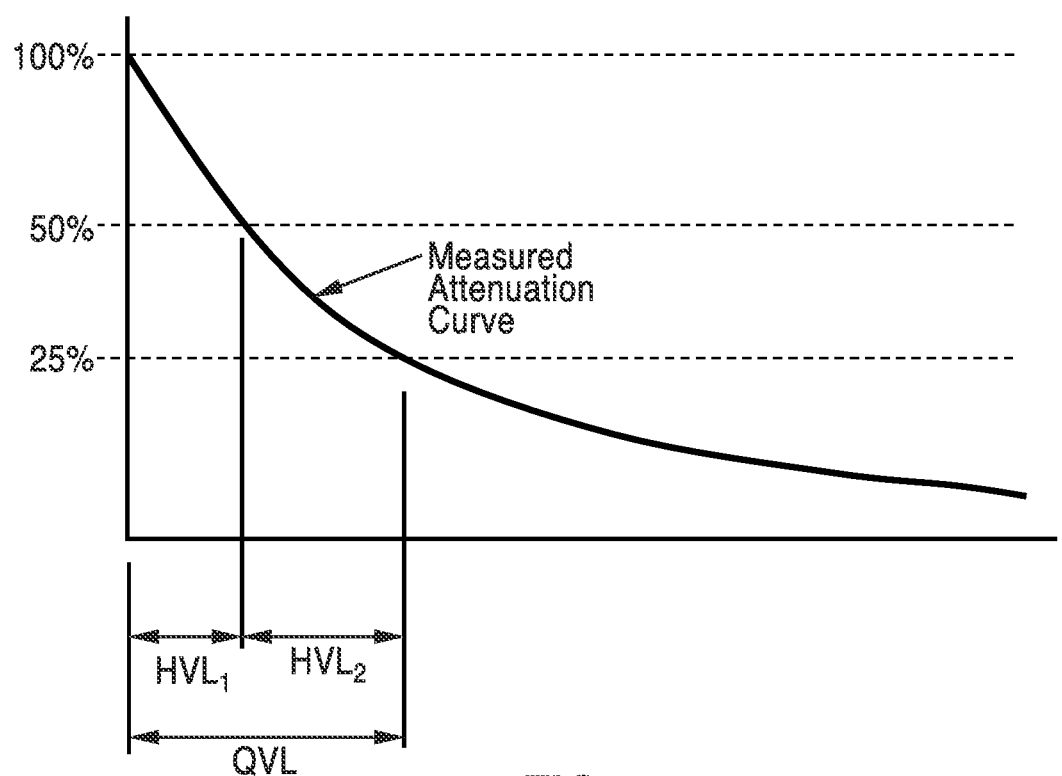
FIG. 9 is a graphical diagram showing that if several metal filters are included on the HVL cage the second half value layer, as shown in this figure, could be determined from the signal trace.

While the measurement of the half value layer (HVL) is a primary metric in the assessment of x-ray beams used in medicine, there is ample literature concerning the assessment of the second half value layer ($HVL_2$). FIG. 9 illustrates the concept of the $HVL_2$. The sum of $HVL_1$ and $HVL_2$ is the quarter value layer (QVL). Thus, a configuration which makes use of a large number of filter thicknesses is conducive to the evaluation of the second HVL.

Figure 10:
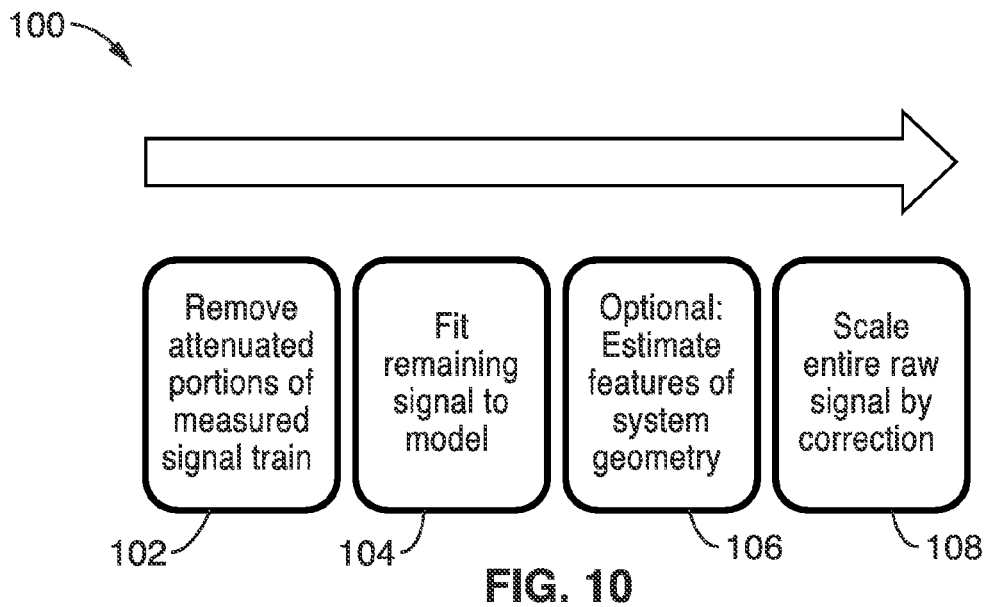
FIG. 10 is a functional flow diagram outlining the correction algorithm for the effects of the inverse square law according to an embodiment of the invention. This correction scheme uses the measured signal from the RT probe to estimate the probe's signal at isocenter, where the source-to-probe distance is constant.
Figure 11:
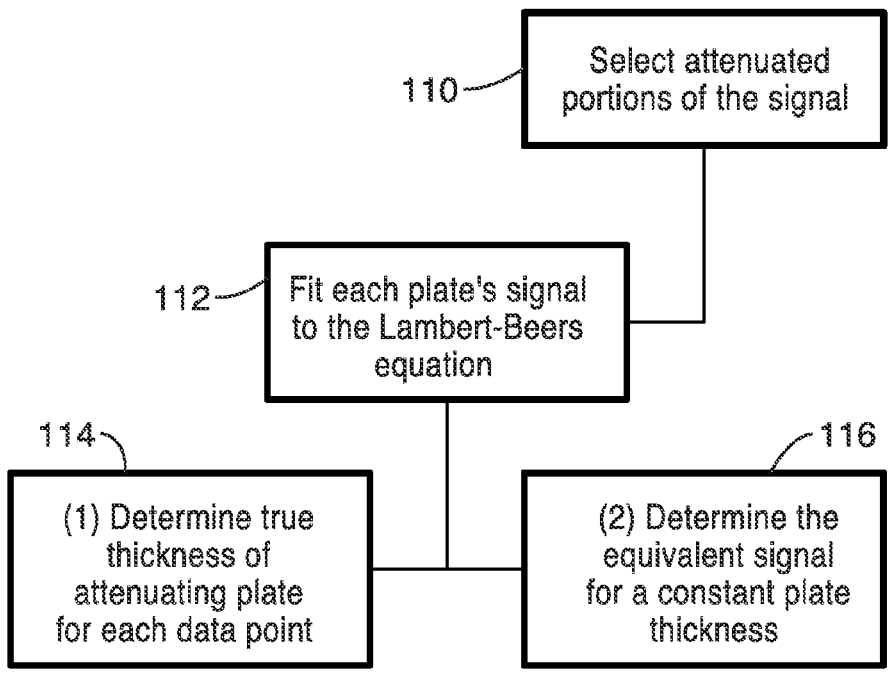
FIG. 11 is a functional flow diagram outlining the correction algorithm for the effects of parallax according to an embodiment of the invention. The correction may either involve (1) using the true thickness of the metal to obtain a spread of relative attenuation measurements or (2) flattening the attenuation hill such that the signal corresponds to a single thickness of the metal filter.

Referring now to FIG. 10 and FIG. 11, there are some apparatus-specific corrections that may be made after the signal is acquired that are due to the physical geometry of the HVL cage. There are two features that may need to be corrected: (A) the cupping effect in the attenuated portions of the signal due to parallax of the planar aluminum plates; and (B) the sinusoidal modulation due to the inverse square law because the source to probe distance changes with time.

As the x-ray beam passes through the filter at an angle, the apparent thickness of the Al decreases as the beam approaches the filter's perpendicular, resulting in a cupped or bowl shaped attenuation profile "hills" across each filter. The bowl shaped signals at the tips of each attenuation measurement adds ambiguity to the overall attenuation value. This effect can be compensated for by (1) making the filters smaller in width, (2) shaping the filters to compensate physically for the parallax issue, or (3) since the geometry of the filter cage is known, software methods can be also be used to correct this problem.

A functional flow diagram 100 outlining the correction algorithm for the effects of the inverse square law according to an embodiment of the invention is shown in FIG. 10. This correction scheme uses the measured signal from the RT probe to estimate the probe's signal at isocenter, where the source-to-probe distance is constant.

The sinusoidal modulation of the RT signal train, most apparent in the unattenuated portions of the beam, is the result of a slight mispositioning of the RT probe from isocenter. This correction is not necessary if the apparatus can be positioned exactly on a system's isocenter; however, this is difficult to achieve in practice. Because the source-to-probe distance is not constant, the measured signal is modulated by the inverse square law (ISL) as the distance increases and decreases during scanner rotation. The periodic behavior of this modulation is a result of the rotational nature of the system set-up.

The ISL correction algorithm consists of four steps: (1) selecting the unattenuated portions of the signal train at block 102; (2) fitting the unattenuated signal to a geometry-based model at block 104; (3) estimating the probe's distance from the source from the fit at block 106; and (4) scaling the probe's output at each time point by the ratio of the probe's distance from the source to the distance from the source to isocenter as block 108. The uncorrected signal, $M_{probe}$, modulated by the ISL as a function of time (t), is given by:

$$M_{probe}(t) = \left(\frac{s^2}{g^2(t)}\right) M_{isocenter}$$

where s is the source-to-isocenter distance, g(t) is the source-to-probe distance, and $M_{isocenter}$ is the signal detected at isocenter. The goal of the correction scheme, outlined in FIG. 10, is to estimate $M_{isocenter}$ from $M_{probe}(t)$.

Because the attenuation of an x-ray beam is spectrally dependent, those regions of the signal train are not useful for determining the ISL correction. Therefore, the first step of the ISL correction is to distinguish the unattenuated signal from the attenuated signal at block 102. There are a variety of methods that can be employed to crop the signal. These methods can range from basic techniques to more computationally advanced procedures. It is possible to simply visually determine the attenuated portions of the signal and manually remove them from the trace. An alternative option is a thresholding technique which is sensitive to the sinusoidal nature of the signal. This can be accomplished through examining the slope between each data point and setting a threshold for an acceptable slope.

Geometric modeling of the unattenuated beam at block 104 assumes that either s or the distance from the probe to isocenter (r), is known, and g(t) must be determined to correct of the ISL effect. Using the system's geometry, it is observed that $$\hat{g}(t) = s^2 + 1 - 2sr\, \cos[\hat{\alpha}(t)]$$

and $$\hat{\alpha}(t) = \frac{2\pi(t - \hat{\delta})}{\hat{\tau}}$$

where α(t) is the angle of rotation, δ is the time point where the probe is closest to the source, and τ is the period of rotation. The carot notation reflects values that must be estimated from the measured signal train. The probe's unattenuated signal can then be modeled by $$\hat{M}_{probe}(t) = \left(\frac{s^2}{s^2 + 1 - 2sr\, \cos[\alpha(t)]}\right) M_{isocenter} \approx \frac{1}{A + B\cos[wt + \phi]}$$

The model's coefficients (A, B, w, and φ) are chosen such that the difference between $\hat{M}_{probe}(t)$ and $M_{probe}(t)$ is minimized. Optionally, the features of the system geometry are estimated at block 106. Several values of the system's geometry must be estimated in order to describe g(t). Either s or r must be known, the other value can then be calculated from the minimum and maximum value of the periodic fit by $$\frac{\hat{M}_{max}}{\hat{M}_{min}} = \frac{(s+r)^2}{(s-r)^2}$$

The phasic and frequency terms can also be calculated by $$\hat{\delta} = t_{max} = \frac{-\phi}{w}$$

and $$\hat{\tau} = \Delta t_{max} = \frac{2\pi}{w}$$

These values can then be plugged into the modeling equations above. It should be noted that while this step is important for fully describing the physical parameters of the system and its set-up, it is not essential for the ISL correction since they are contained within the model of g(t). Correction of the entire raw signal train is scaled at block 108. Using the system's geometry calculated at block 106, the corrected signal can be calculated as $$\hat{M}_{isocenter}(t) = \left(\frac{\hat{g}^2(t)}{s^2}\right) M_{probe}(t)$$

Alternatively, the corrected signal can be equivalently calculated directly from $\hat{M}_{probe}(t)$ by scaling and shifting the measured signal by $$\hat{M}_{isocenter}(t) = A \frac{M_{probe}(t)}{\hat{M}_{probe}(t)}$$

Turning now to FIG. 11, a functional flow diagram outlining the correction algorithm for the effects of parallax is shown according to an embodiment of the invention. The correction may either involve (1) using the true thickness of the metal to obtain a spread of relative attenuation measurements or (2) flattening the attenuation hill such that the signal corresponds to a single thickness of the metal filter.

The observed attenuation "hills" of the RT signal train that is the result of parallax from the aluminum plates can be corrected. When the x-ray source is normal to an aluminum plate, it is attenuated the least. As the source rotates through an angle θ, the x-ray beam is increasingly attenuated by the aluminum plate, resulting in a lower signal. Of course, one obvious solution is to avoid the parallax problem completely and use curved aluminum plates such that the x-ray beam is attenuated by a constant thickness of aluminum.

Given that the attenuating plates for the HVL cage are planar, there are two preferred ways to correct the signal parallax, which are outlined in FIG. 11.

1) Directly account for the increase of the plate's thickness in those portions of the signal. Instead of obtaining a single relative attenuation value for a given thickness of aluminum $x_{Al}$, there will be a spread of relative attenuation values for $x_{Al}+\Delta x_{Al}$, where $\Delta x_{Al}$ is the extra material that the beam travels through.

2) Correct the attenuation data such that it can be averaged to a single relative attenuation value for a plate of aluminum.

At block 110 of FIG. 11, the first step in the parallax correction is to identify attenuated portions of the signal train. As described previously, there are a variety of useful techniques that crop the signal train. In this case, the attenuated signal will vary significantly with each metal plate. It is fairly trivial to match an attenuation "hill" with its corresponding aluminum plate.

At block 112, the attenuated beam is preferably modeled to fit the Lambert-Beers equation. The attenuated beam for a normal x-ray beam to a plate of thickness $x_{Al}$ can be described with the Lambert-Beers equation $$M_{normal}=M_0 e^{-\mu_{Al} x_{Al}}$$

where $M_0$ is the unattenuated signal and $\mu_{Al}$ is the linear attenuation of aluminum. For other source positions, the detected beam can be described as $$\hat{M}_{probe}(t) = M_0 e^{-\frac{\mu_{A1} x_{A1}}{\cos(\alpha t)}} \sim A e^{\frac{\beta}{\cos(wt+\varphi)}}$$

The model's coefficients (β, w, and φ) are chosen to minimize the difference between $\hat{M}_{probe}(t)$ and $M_{probe}(t)$.

There are two preferred options for applying a correction shown in FIG. 11. Option 1 at block 114: Using the model's values of w and φ, $x_{Al}+\Delta x_{Al}$ can be determined for each time point by:

$$x_{A1} + \Delta x_{A1}(t) = \frac{x_{A1}}{\cos(wt+\varphi)}$$

Again, this means that each relative attenuation data point determined from $M_{probe}(t)$ will correspond to a slightly different thickness of aluminum, but these values will still fall along the same relative attenuation curve.

Option 2 at block 116: Using the model's values of β, w, and φ, an estimate of the probe's signal at $x_{Al}$ (defined as $\hat{M}_{Normal}$) can be determined. To do this, the effect of $\Delta x_{Al}$ must be removed from the measured signal such that $$\hat{M}_{normal}=M_{probe}(t)e^{+\mu \Delta x_{Al}}$$

Using the values from the fit, we find $$\hat{M}_{normal} \approx M_{probe}(t)e^{\left(\frac{\beta}{\cos(wt+\varphi)}-\beta\right)}$$

With this correction, all values from an attenuation "hill" collapse to a single point. This allows for averaging and additional denoising techniques.

To follow through with this analysis, the relative attenuation and HVL of an acquired signal is plotted. The relative attenuation is determined from the ratio of the corrected attenuated signal to the average of the probe's corrected unattenuated signal. Conventional HVL estimate techniques are then employed to determine the amount of aluminum necessary to attenuate the x-ray beam by 50%.

The invention may be better understood with reference to the accompanying example, which is intended for purpose of illustration only and should not be construed as in any sense limiting the scope of the present invention as defined in the claims appended hereto.

EXAMPLE

To demonstrate the functionality of the system, a cage was constructed with aluminum plates. The plates around the probe are of different thicknesses; the active area of the dose probe is near the tip of the probe and centered within the ring of plates. As the CT source rotated around the HVL apparatus the beam was attenuated to varying degrees and the signal train of the RT probe reflected these differences in beam attenuation.

Real-time (RT) measurements were obtained using a prototype RT dose probe from Diagnostic Imaging Specialists Corp (DISC). The active area of the probe was a small cylindrical solid-state scintillator with a height of 5 mm and a diameter of 5 mm; the manufacturers reported sampling rate was under 1 kHz. Previously, the probe was shown to have an isotropic response to incident x-rays.

The response of the RT probe to a variety of x-ray spectra, ranging from 50 kVp to 120 kVp in intervals of 10 kVp, was measured and confirmed to be linear. Sister measurements were conducted using a general purpose Radcal 9010 ion chamber at the same position as the RT prototype probe. The measurements were then compared to those made by the RT probe. A linear fit of the data was used to estimate the response of the RT probe at a fixed ion chamber response across the series of x-ray tube potentials A signal train was obtained from the RT probe in the HVL apparatus. The low-frequency sinusoidal component of the signal is a result of not positioning the probe exactly at isocenter such that the source is not exactly the same distance from the probe as it completes a scan. A correction for the effects of the inverse square law was made using the unattenuated data.

X-ray beam quality is a key factor to consider when estimating dose to a patient; unfortunately, beam quality is difficult to directly measure on current commercial clinical CT scanners. The method to measure the half value layer (HVL)

of a clinical CT scanner using a prototype real-time dose probe and prototype HVL apparatus was demonstrated.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. An apparatus for half value layer measurement, comprising: a cage structure; the cage structure having a central axis; the cage structure having a central opening defined by a filter encircling the central axis; the filter having a thickness that varies peripherally around the central axis.

2. The apparatus of embodiment 1, wherein the filter comprises a cylinder having sidewalls with continuously increasing thickness.

3. The apparatus of embodiment 1, wherein the filter comprises a plurality of spaced-apart plates having varying thicknesses.

4. The apparatus of embodiment 3, wherein the plurality of plates comprises approximately five plates to approximately ten plates.

5. The apparatus of embodiment 3, wherein the plurality of plates comprises eight plates arranged in an octagonal pattern.

6. The apparatus of embodiment 1, further comprising a probe holder attached to the cage; wherein the probe holder is configured to retain at least a portion of the probe within the central opening of the cage.

7. The apparatus of embodiment 1, wherein the filter is fabricated from a metal selected from the group of metals consisting of aluminum, copper and tin.

8. The apparatus of embodiment 3, further comprising: attenuating septa mounted between the plates radiating inwardly in the central opening of the cage; wherein scattered radiation from adjacent plates of the cage is attenuated.

9. The apparatus of embodiment 8, wherein the septa are fabricated from lead or tungsten.

10. The apparatus of embodiment 1, further comprising: a radiation probe mounted in the central axis of the cage; an elongate boom, the boom mounted to the cage and to a cart; wherein the central axis of the cage and the radiation probe are configured for disposition in the center of a orbital source of x-rays.

11. The apparatus of embodiment 10, the cart further comprising: a computer with computer programming operably coupled to the radiation probe; wherein signals from the radiation probe are processed and recorded by the computer and computer programming.

12. The apparatus of embodiment 10, wherein the boom is configured to reversibly mount to a cage; wherein cages with different plate configurations are interchangeable and reversibly mounted to the boom.

13. An apparatus for half value layer measurement, comprising: a cage structure with an open interior with a plurality of spaced-apart plates having varying thicknesses and with a proximal end of each plate coupled to a first support wall and a distal end of each plate coupled to a second support wall; the cage structure having a central axis; a radiation probe disposed in the interior of the cage structure; and a motor and controller operably coupled to the cage; wherein the cage is capable of axial rotation around the central axis at speeds controlled by the controller.

14. The apparatus of embodiment 13, wherein the plates of the cage structure range in thickness from 0.1 mm to 15 mm.

15. The apparatus of embodiment 13, further comprising: a collimator, the collimator disposed between the cage and a source of x-rays.

16. The apparatus of embodiment 13, further comprising: attenuating septa mounted between the plates radiating inwardly in the central opening of the cage; wherein scattered radiation from adjacent plates of the cage is attenuated.

17. A method for half value layer measurements, comprising: acquiring a signal train from a radiation probe in a central axis of a cage having a central opening defined by a filter encircling the central axis; the filter having a thickness that varies peripherally around the central axis and a source of x-rays; processing the acquired signal to correct cupping effect in the attenuated portions of the signal due to parallax of the planar filter plates; processing the acquired signal to correct sinusoidal modulation due to the inverse square law because the source to probe distance changes with time; and formulating a half value layer from the processed signal.

18. The method of embodiment 17, wherein the processing of the signal to correct effects due to parallax of the planar filter plates comprises: selecting attenuated portions of the signal; fitting the signal from each plate to a Lambert-Beers equation; and determining a true thickness of a plate for each data point.

19. The method of embodiment 17, wherein the processing of the signal to correct effects due to parallax of the planar filter plates comprises: selecting attenuated portions of the signal; fitting the signal from each plate to a Lambert-Beers equation; and determining an equivalent signal for a constant plate thickness.

20. The method of embodiment 17, wherein the processing of the signal to correct sinusoidal modulation due to the inverse square law, comprises: selecting the unattenuated portions of the signal train; fitting the unattenuated signal to a geometry-based model; estimating the probe's distance from a source from fit; and scaling the probe's output at each time point by the ratio of the probe's distance from the source to isocenter Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for half value layer measurement, comprising:
    a cage structure;
    said cage structure having a central axis; and
    a filter encircling said central axis;
    said cage structure having a central opening defined by said filter;
    said filter having a thickness that varies peripherally around said central axis.

2. An apparatus as recited in claim 1, wherein said filter comprises a cylinder having sidewalls with continuously increasing thickness.

3. An apparatus as recited in claim 1, wherein said filter comprises a plurality of spaced-apart plates having varying thicknesses.

4. An apparatus as recited in claim 3, wherein said plurality of plates comprises approximately five plates to approximately ten plates.

5. An apparatus as recited in claim 3, wherein said plurality of plates comprises eight plates arranged in an octagonal pattern.

6. An apparatus as recited in claim 1, further comprising:
    a probe holder attached to the cage;
    wherein said probe holder is configured to retain at least a portion of the probe within the central opening of the cage.

7. An apparatus as recited in claim 1, wherein the filter is fabricated from a metal selected from the group of metals consisting of aluminum, copper and tin.

8. An apparatus as recited in claim 3, further comprising:
    attenuating septa mounted between said plates radiating inwardly in the central opening of said cage;
    wherein scattered radiation from adjacent plates of said cage is attenuated.

9. An apparatus as recited in claim 8, wherein the septa are fabricated from lead or tungsten.

10. An apparatus as recited in claim 1, further comprising:
    a radiation probe mounted in the central axis of the cage;
    an elongate boom, the boom mounted to the cage and to a cart;
    wherein the central axis of the cage and the radiation probe are configured for disposition in the center of a orbital source of x-rays.

11. An apparatus as recited in claim 10, said cart further comprising:
    a computer with computer programming operably coupled to the radiation probe;
    wherein signals from the radiation probe are processed and recorded by the computer and computer programming.

12. An apparatus as recited in claim 10, wherein the boom is configured to reversibly mount to a cage;
    wherein cages with different plate configurations are interchangeable and reversibly mounted to the boom.

13. An apparatus for half value layer measurement, comprising:
    a cage structure with an open interior with a plurality of spaced-apart plates having varying thicknesses and a proximal end of each plate coupled to a first support wall and a distal end of each plate coupled to a second support wall;
    said cage structure having a central axis;
    a radiation probe disposed in the interior of the cage structure; and
    a motor and controller operably coupled to the cage;
    wherein the cage is capable of axial rotation around the central axis at speeds controlled by the controller.

14. An apparatus as recited in claim 13, wherein the plates of the cage structure range in thickness from 0.1 mm to 15 mm.

15. An apparatus as recited in claim 13, further comprising:
    a collimator, the collimator disposed between the cage and a source of x-rays.

16. An apparatus as recited in claim 13, further comprising:
    attenuating septa mounted between said plates radiating inwardly in the central opening of said cage;
    wherein scattered radiation from adjacent plates of said cage is attenuated.

17. A method for half value layer measurements, comprising:
    acquiring a signal train from a radiation probe in a central axis of a cage having a central opening defined by a filter encircling said central axis, the filter having a thickness that varies peripherally around the central axis and a source of x-rays;
    processing the acquired signal to correct cupping effects in the attenuated portions of the signal due to parallax of planar filter plates;

processing the acquired signal to correct sinusoidal modulation due to the inverse square law because the source to probe distance changes with time; and formulating a half value layer from the processed signal.

18. A method as recited in claim 17, wherein the processing of the signal to correct effects due to parallax of the planar filter plates comprises:

selecting attenuated portions of the signal;

fitting the signal from each plate to a Lambert-Beers equation; and determining a true thickness of a plate for each data point.

19. A method as recited in claim 17, wherein the processing of the signal to correct effects due to parallax of the planar filter plates comprises:

selecting attenuated portions of the signal;

fitting the signal from each plate to a Lambert-Beers equation; and determining an equivalent signal for a constant plate thickness.

20. A method as recited in claim 17, wherein the processing of the signal to correct sinusoidal modulation due to the inverse square law, comprises:

selecting the unattenuated protions of the signal train;

fitting unattenuated signal to a geometry-based model;

estimating the probe's distance from a source from fit; and scaling the probe's output at each time point by the ratio of the probe's distance from the source to isocenter.

\* \* \* \* \*